United States Patent

Jäger et al.

Patent Number: 4,731,452
Date of Patent: * Mar. 15, 1988

[54] PREPARATION OF NOVEL AZOLYLMETHYL KETONES

[75] Inventors: Gerhard Jäger, Leverkusen; Manfred Jautelat, Burscheid; Wolfgang Krämer, Wuppertal, all of Fed. Rep. of Germany

[73] Assignee: Bayer Aktiengesellschaft, Leverkusen, Fed. Rep. of Germany

[*] Notice: The portion of the term of this patent subsequent to Oct. 29, 2002 has been disclaimed.

[21] Appl. No.: 498,605

[22] Filed: May 27, 1983

[30] Foreign Application Priority Data

Jun. 12, 1982 [DE] Fed. Rep. of Germany ....... 3222220

[51] Int. Cl.$^4$ .................. C07D 249/04; C07D 233/60
[52] U.S. Cl. .................................... 548/262; 548/341
[58] Field of Search ............................... 548/262, 341

[56] References Cited

U.S. PATENT DOCUMENTS

| 4,079,143 | 3/1978 | Balasubramanyan, II et al. | 424/269 |
|---|---|---|---|
| 4,451,281 | 5/1984 | Elbe et al. | 548/262 |
| 4,549,900 | 10/1985 | Kramer et al. | 548/101 |

FOREIGN PATENT DOCUMENTS

| 2737489 | 2/1978 | Fed. Rep. of Germany | 424/269 |
|---|---|---|---|
| 2833194 | 2/1980 | Fed. Rep. of Germany | 548/262 |
| 2929602 | 2/1981 | Fed. Rep. of Germany | 542/458 |
| 2937595 | 4/1981 | Fed. Rep. of Germany | 548/262 |
| 3028330 | 4/1982 | Fed. Rep. of Germany | 542/458 |

*Primary Examiner*—Glennon H. Hollrah
*Assistant Examiner*—D. L. Dinner
*Attorney, Agent, or Firm*—Sprung Horn Kramer & Woods

[57] ABSTRACT

Azolylmethyl ketones of the formula

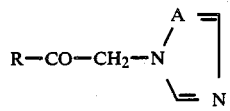

in which
A is a nitrogen atom or the CH group,
R is adamantyl, or the group

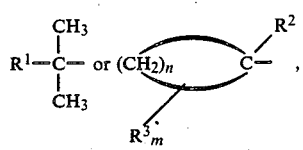

$R^1$ is neopentyl, optionally substituted phenoxyethyl or cyanoethyl,
$R^2$ is alkyl,
$R^3$ is alkyl or halogen,
n is 3, 4, 5, 6 or 7, and
m is 1, 2, or 3, are useful as intermediates in making fungicidally active compounds of the formula

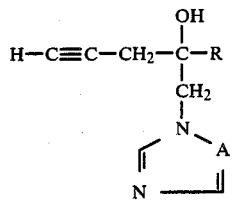

4 Claims, No Drawings

PREPARATION OF NOVEL AZOLYLMETHYL KETONES

The present invention relates to new azolylmethyl ketones, a process for their preparation and their use as intermediate products for the synthesis of hydroxyalkinylazolyl derivatives which have fungicidal properties.

It has already been disclosed that certain hydroxyalkyltriazoles, such as, for example, 2-(4-biphenylyl)-1-(2,4-dichlorophenyl)-3-(1,2,4-triazol-1-yl)-2-propanol or 2-(4-biphenylyl)-1-(4-chlorophenyl)-3-(1,2,4-triazol-1-yl)-2-propanol have fungicidal properties (compare U.S. application Ser. No. 144,102, filed Apr. 28, 1980, abandoned). However, the activity of these compounds is not always entirely satisfactory, especially when low amounts and concentrations are applied.

New azolylmethyl ketones of the formula

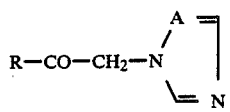   (I)

in which
A represents a nitrogen atom or the CH group,
R represents adamantyl or the groups

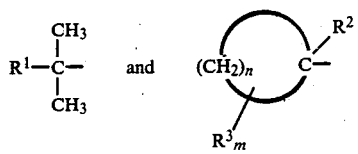

wherein
$R^1$ represents neopentyl, optionally substituted phenoxyethyl or cyanoethyl,
$R^2$ represents alkyl,
$R^3$ represents alkyl or halogen,
n represents the numbers 3, 4, 5, 6 and 7 and
m represents the numbers 1, 2 and 3,
have been found.

Moreover, it has been found that the new azolylmethyl ketones of the formula (I) are obtained by reacting, in the presence of a diluent and in the presence of an acid-binding agent, halogenomethyl ketones of the formula $$R-CO-CH_2-Hal \qquad (II)$$

in which
R has the abovementioned meaning and
Hal represents chlorine or bromine,
with azoles of the formula

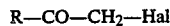   (III)

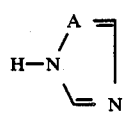

in which
A has the abovementioned meaning.

The new azolylmethyl ketones are interesting intermediate products for the preparation of active compounds for plant protection. Thus, the materials of the formula (I) are suitable as starting materials for the synthesis of hydroxyalkinylazolyl derivatives which have very good fungicidal activity.

Surprisingly, the hydroxyalkinylazolyl derivatives, which can be prepared from the azolylmethyl ketones of the formula (I) according to the invention, for example by reaction with propargyl halides in the presence of activated aluminum are superior in respect of their fungicidal activity to the compounds 2-(4-biphenylyl)-1-(2,4-dichlorophenyl)-3-(1,2,4-triazol-1-yl)-2-propanol and 2-(4-biphenylyl)-1-(4-chlorophenyl)-3-(1,2,4-triazol-1-yl)-2-propanol known from the state of the art.

The materials according to the invention are generally defined by the formula (I). In this formula,
R preferably represents adamantyl or the groups

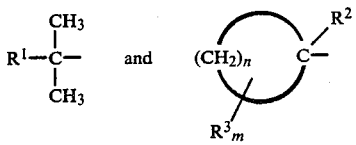

$R^1$ preferably represents neopentyl, cyanoethyl or phenoxyethyl, which optionally has one to three identical or different substituents, the preferred phenyl substituents which may be mentioned being: halogen, alkyl having 1 to 4 carbon atoms, alkoxy and alkylthio, each having 1 to 2 carbon atoms, halogenoalkyl, halogenoalkoxy and halogenoalkylthio, each having 1 to 2 carbon atoms and 1 to 5 identical or different halogen atoms, such as, preferably, fluorine and chlorine atoms, cyclohexyl, dialkylamino having 1 to 4 carbon atoms in each alkyl moiety, nitro, cyano and alkoxycarbonyl having 1 to 4 carbon atoms in the alkyl moiety and phenyl or phenoxy which is optionally substituted by halogen;
$R^2$ preferably represents straight-chain or branched alkyl having 1 to 6 carbon atoms;
$R^3$ preferably represents straight-chain or branched alkyl having 1 to 4 carbon atoms, chlorine or bromine;
m preferably represents the numbers 1 or 2; and
A and n preferably represent the meanings mentioned in the definition of the invention.

Those compounds of the formula (I) are particularly preferred in which
R represents adamantyl or the groups

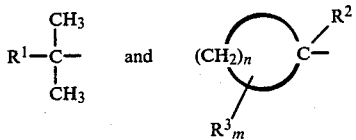

$R^1$ represents neopentyl, cyanoethyl or phenoxyethyl, which optionally has one to two identical or different substituents, the phenyl substituents which may be mentioned being: fluorine, chlorine, bromine, methyl, ethyl, isopropyl, tert.-butyl, methoxy, ethoxy, methylthio, trifluoromethyl, trifluoromethoxy, trifluoromethylthio, nitro, dimethylamino, methoxycarbonyl and phenyl or phenoxy which is optionally substituted by chlorine;
$R^2$ represents methyl or ethyl;
$R^3$ represents methyl, ethyl, isopropyl, tert.-butyl or chlorine;

m represents the numbers 1 or 2; and

A and n represent the meanings mentioned in the definition of the invention.

In particular, apart from the compounds mentioned in the preparation examples, the following compounds of the formula (I) may be mentioned (A represents both a nitrogen atom and a CH group):

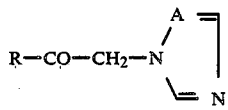
(I)

| R | R |
|---|---|
| 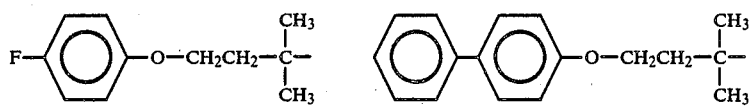 | |
| 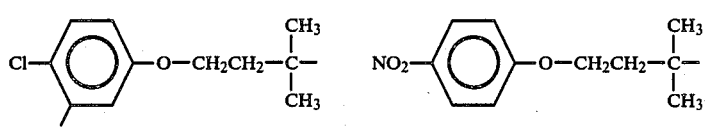 | |
| 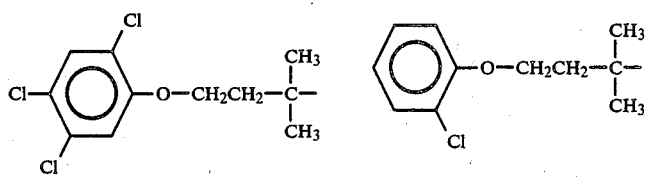 | |
| 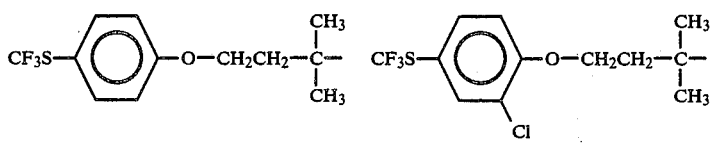 | |
|  | |
| 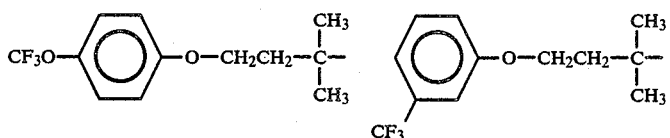 | |

-continued

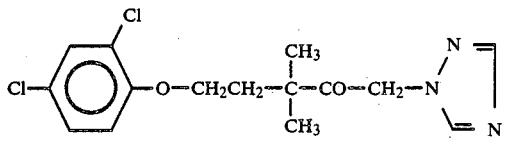

When, for example, 1-chloro-5-(2,4-dichlorophenoxy)-3,3-dimethyl-2-pentanone and 1,2,4-triazole are used as starting materials, the course of reaction in the process according to the invention can be represented by the following scheme:

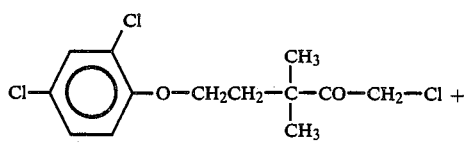

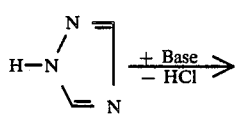

The halogenomethyl ketones necessary as starting materials for carrying out the process according to the invention are generally defined by the formula (II). In this formula, R preferably represents those meanings which have already preferably been mentioned for these substituents in connection with the description of the materials of the formula (I) according to the invention.

Some of the halogenomethyl ketones of the formula (II) are known (U.S. application Ser. No. 329,959, filed Dec. 11, 1981, pending.) They can be prepared in a simple manner by known processes, by reacting appropriate methyl ketones in a customary manner with chlorine or bromine in the presence of an inert organic solvent, such as, for example, ethers, chlorinated or nonchlorinated hydrocarbons, at room temperature, or with customary chlorinating agents, such as, for example, sulphuryl chloride, at 20° to 60° C.

The halogenomethyl ketones of the formula (II) can also be obtained by reacting, in the presence of an inert organic solvent, such as, for example, dimethylformamide, at temperatures between 100° to 220° C., optionally under elevated pressure, 1,1-dichloroalkenes of the formula R'—CH=CCl$_2$ (IV)

in which
R' represents R or the group Cl—CH$_2$CH$_2$—C(CH$_3$)$_2$,
with phenols of the formula

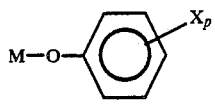

(V)

in which
M represents one equivalent of an alkali metal or alkaline earth metal ion, especially a sodium or potassium ion,
X represents halogen, alkyl or alkoxy, each having 1 to 3 carbon atoms, or phenyl and
p represents the numbers 0, 1 or 2,
and hydrolyzing, in a customary manner with mineral acids, such as, for example, sulphuric acid or hydrochloric acid, and/or with organic acids, such as, for example, formic acid, at 40° to 100° C., the phenyl ethers thus obtained of the formula

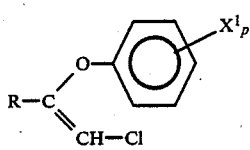

(VI)

in which
R, X$^1$ and p have the abovementioned meanings.

The preparation of 1,1-dichloroalkenes of the formula (IV) is known. It is accomplished by addition of alkyl halides to vinylidene chloride in the presence of acid catalysts (in this context, compare J. Am. Chem. Soc. 74, 2885 (1962)), with hydrogen halide being split off simultaneously.

Inert organic solvents are suitable as diluents for the process according to the invention. These include, preferably, ketones, such as acetone, methyl ethyl ketone and methyl butyl ketone; alcohols, such as ethanol, isopropanol and butanol; aromatic hydrocarbons, such as benzene and toluene; formamides and sulphoxides, such as dimethylformamide and dimethyl sulphoxide.

The process according to the invention is carried out in the presence of an acid-binding agent. It is possible to add all inorganic or organic acid binders which can customarily be used, such as alkali metal carbonates, for example sodium carbonate, potassium carbonate and sodium bicarbonate, such as alkali metal and alkaline earth metal hydroxides, for example potassium hydroxide and calcium hydroxide, or such as lower tertiary alkylamines, cycloalkylamines or aralkylamines, for example triethylamine, N,N-dimethylcyclohexylamine, dicyclohexylamine, N,N-dimethylbenzylamine and pyridine and diazabicyclooctane, and also an appropriate excess of azole.

The reaction temperatures for the process according to the invention can be varied within a relatively wide range. It is generally carried out at temperatures between 0° and 120° C., preferably between 20°0 and 90° C. It is advantageously carried out at the boiling point of the particular solvent.

In carrying out the process according to the invention, preferably 1 to 4 mols of azole and 1 to 4 mols of acid binder are employed for 1 mol of the compounds of the formula (II). In order to isolate the compounds of the formula (I), the solvent is distilled off and the residue is worked up in a customary manner.

The azolylmethyl ketones of the formula (I) according to the invention are suitable as intermediate products for the synthesis of hydroxyalkinylazolyl derivatives which have fungicidal activity.

Hydroxyalkinylazolyl derivatives of this type, of the formula

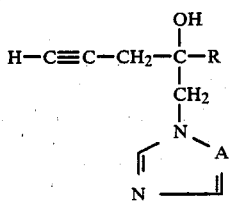

(VII)

in which
A and R have the abovementioned meanings,
can be prepared by, for example, reacting, in the presence of activated aluminum and in the presence of a diluent, azolylmethyl ketones of the formula

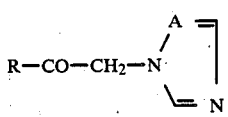

(I)

in which
A and R have the abovementioned meanings,
with propargyl halides of the formula HC≡C—CH$_2$—Hal' (VIII)

in which
Hal' represents chlorine or bromine.

Suitable diluents for the reaction of the azolylmethyl ketones of the formula (I) according to the invention with propargyl halides of the formula (VIII) are organic, aprotic solvents, such as, for example, diethyl ether or tetrahydrofuran.

The process mentioned above for the preparation of hydroxyalkinylazolyl derivatives (VII) is carried out in the presence of activated aluminum. This activation is brought about by the addition of catalytic amounts of mercury (II) chloride and iodine.

In the abovementioned process for the preparation of hydroxyalkinylazolyl derivatives, the reaction temperature can be varied within a relatively wide range. It is generally carried out at temperatures between −80° and +100° C., preferably between −70° and +60° C.

In carrying out the abovementioned process for the preparation of hydroxyalkinylazolyl derivatives (VII), 1 to 2 mols of propargyl halide of the formula (VIII)

and 1 to 1.5 mols of aluminum together with catalytic amounts of mercury(II) chloride and iodine are employed for 1 mol of azolylmethyl ketone of the formula (I). The compounds of the formula (VII) are isolated in a customary manner.

The hydroxyalkinylazolyl derivatives of the formula (VII) which can be prepared from the materials according to the invention have very good fungicidal properties.

PREPARATION EXAMPLES
EXAMPLE 1

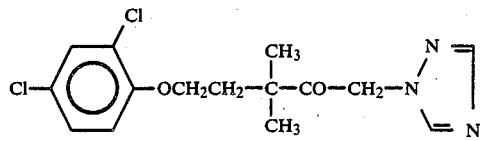

30.9 g (0.1 mol) of 1-chloro-5-(2,4-dichlorophenoxy)-3,3-dimethyl-2-pentanone, dissolved in 80 ml of acetone, are added dropwise, with stirring, to a mixture of 13.8 g (0.1 mol) of potassium carbonate and 13.8 g (0.2 mol) of 1,2,4-triazole in 200 ml of boiling acetone. The mixture is boiled for a further 3 hours, cooled down to 0° to 10° C., the salt is filtered off and the filtrate is evaporated in vacuo. After trituration of the oily residue with a little petroleum ether, 32.4 g (94.6% of theory) of 5-(2,4-dichlorophenoxy)-3,3-dimethyl-1-(1,2,4-triazol-1-yl)-2-pentanone are obtained as colorless crystals of melting point 62° C.

Preparation of the starting product

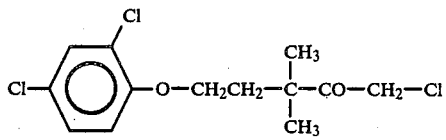

454 g (1 mol) of 1-chloro-3,3-dimethyl-2,5-di(2,4-dichlorophenoxy)-1-pentene in 500 ml of formic acid and 50 ml of concentrated hydrochloric acid are heated at 100° C. for 9 hours. The mixture is diluted with methylene chloride and extracted by shaking once with water and three times with dilute sodium hydroxide solution. After drying the solution, the solvent is removed in vacuo. 238 g (77% of theory) of crude 5-(2,4-dichlorophenoxy)-3,3-dimethyl-2-pentanone, which slowly crystallizes, are obtained. After washing with petroleum ether, the product has a melting point of 55°–58° C.

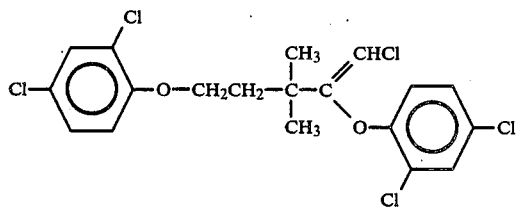

489 g (3 mols) of 2,4-dichlorophenol are dissolved in 1.2 liters of N-methylpyrrolidone, and 600 ml (3 mols) of a 30% strength solution of sodium methylate are added. Methanol and 200 ml of N-methylpyrrolidone are distilled off at 20 mbar. 201 g (1 mol) of 1,1,5-trichloro-3,3-dimethyl-1-pentene are slowly added dropwise at 200° C. and atmospheric pressure. The mixture is then stirred at 200° C. for 6 hours. The solution obtained is diluted with methylene chloride and extracted by shaking several times with dilute sodium hydroxide solution. The dried solution is evaporated and the remaining solvent removed at 0.1 mbar and 150° C. 410 g (90% of theory) of 1-chloro-3,3-dimethyl-1,5-di(2,4-dichlorophenoxy)-1-pentene are obtained as an oil.

NMR (CDCl$_3$): δ=1.2 (s, 6H), 2.1 (t, 2H, J=7 Hz), 4.1 (t, 2H, J=7 Hz), 5.95 (s, 1H), 6.75–7.4 (m, 6H).

EXAMPLE 2

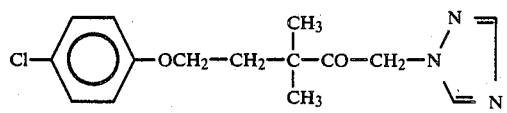

A solution of 55 g (0.2 mol) of 1-chloro-5-(4-chlorophenoxy)-3,3-dimethyl-2-pentanone in 50 ml of acetone is added dropwise to a mixture of 27.6 g (0.2 mol) of potassium carbonate and 27.6 g (0.4 mol) of 1,2,4-triazole in 400 ml of boiling acetone. The mixture is boiled for a further 3 hours, cooled down to 20° C., filtered and the filtrate is evaporated in vacuo. The oily residue is taken up in 250 ml of ethyl acetate and washed three times with 100 ml of water each time. After drying the organic phase over anhydrous sodium sulphate, it is evaporated in vacupo. the residual crude product (61 g) is dissolved in 250 ml of acetone, and a solution of 57.6 g of naphthalene-1,5-disulphonic acid in 250 ml of acetone is added. The salt which has crystallized out (45.4 g; melting point 188°–190° C.) is suspended in a mixture of 150 ml each of dichloromethane and water and is made alkaline by the addition of 10% strength sodium carbonate solution. The organic phase is separated off, and the aqueous phase is extracted once more with 100 ml of dichloromethane and the combined organic phases are evaporated in vacuo. 30.4 g (49.4% of theory) of 5-(4-chlorophenoxy)-3,3-dimethyl-1-(1,2,4-triazol-1-yl)-2-pentanone are obtained as a pale yellowish liquid of refractive index $n_D{}^{20}$=1.5457.

Preparation of the starting product

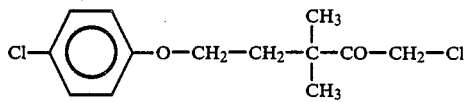

580 g (1.5 mols) of 1-chloro-3,3-dimethyl-1,5-di-(4-chlorophenoxy)-1-pentene in 1,000 ml of ethanol and 300 ml of concentrated hydrochloric acid are heated under reflux for 4 hours. The ethanol is removed in vacuo, and the residue is diluted with methylene chloride and extracted by shaking with water, and then three times with dilute sodium hydroxide solution. The dried solution is freed of solvent in vacuo. 363 g (88% of theory) of 1-chloro-5-(4-chlorophenoxy)-3,3-dimethyl-2-pentanone are obtained as an oil.

NMR (CDCl$_3$): δ=1.25 (s, 6H), 2.1 (t, 2H, J=6 Hz), 3.9 (t, 2H, J=6 Hz), 4.45 (s, 2H), 6.7–7.3 (m, 4H)

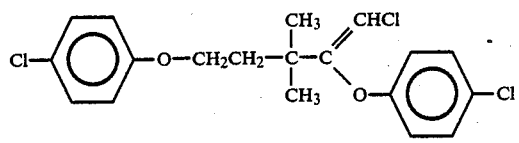

771 g (6 mols) of chlorophenol are dissolved in 2.4 liters of dimethylformamide, and 1.2 liters (6 mols) of 30% strength sodium methylate solution are added. The methanol is removed in vacuo and about 400 ml of dimethylformamide are also distilled off at 20 mbar. Then, at 150° C., 403 g (2 mols) of 1,1,5-trichloro-3,3-dimethyl-1-pentene are slowly added dropwise and the mixture is heated under reflux for 8 hours. Working up takes place with methylene chloride and water and dilute sodium hydroxide solution. After removing the solvent in vacuo, initial distillation is carried out at 0.1 mbar and 150° C. 646 (84% of theory) of 1-chloro-3,3-dimethyl-2,5-di(4-chlorophenoxy)-1-pentene are obtained as an oil.

NMR (CDCl#3$): $\delta$=1.2 (s, 6H), 2.0 (t, 2H, J=7 Hz), 4.0 (t, 2H, 7 Hz), 5.9 (s, 1H), 6.75–7.35 ppm (m, 8H).

In an analogous manner, and in accordance with the process according to the invention, the compounds listed below of the formula

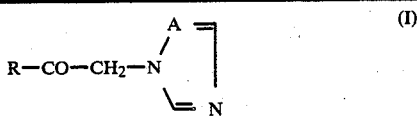

are obtained:

| Example No. | R | A | Melting point (°C.) or refractive index $n_D^{20}$ |
|---|---|---|---|
| 3 | ⌬—O—CH₂CH₂—C(CH₃)₂— | N | Resin |
| 4 | 2,4-Cl₂-C₆H₃—OCH₂CH₂—C(CH₃)₂— | CH | 46–48 |
| 5 | Adamantyl | N | 129 |
| 6 | (CH₃)₃C—CH₂—C(CH₃)₂— | N | 1.4851 |
| 7 | (CH₃)₃C—CH₂—C(CH₃)₂— | CH | 54–56 |
| 8 | i-C₃H₇—cyclohexyl(CH₃)— | N | 99–101 |
| 9 | biphenyl-OCH₂CH₂—C(CH₃)₂— | CH | 132–34 |
| 10 | biphenyl-OCH₂CH₂—C(CH₃)₂— | N | 125–27 |
| 11 | 4-F-C₆H₄—OCH₂CH₂—C(CH₃)₂— | CH | 1.5290 |
| 12 | 4-F-C₆H₄—OCH₂CH₂—C(CH₃)₂— | N | 1.5238 |
| 13 | 3-Cl-4-F-C₆H₃—O—CH₂CH₂—C(CH₃)₂— | CH | 69–70 |
| 14 | 3-Cl-4-F-C₆H₃—O—CH₂CH₂—C(CH₃)₂— | N | 54–56 |
| 15 | 4-CF₃S-C₆H₄—O—CH₂CH₂—C(CH₃)₂— | CH | 1.5233 |
| 16 | 4-CF₃S-C₆H₄—O—CH₂CH₂—C(CH₃)₂— | N | 72–77 |
| 17 | 3-CF₃-C₆H₄—O—CH₂CH₂—C(CH₃)₂— | CH | 1.5025 |
| 18 | 4-CF₃O-C₆H₄—O—CH₂CH₂—C(CH₃)₂— | CH | 1.4939 |
| 19 | 2-Cl-C₆H₄—O—CH₂CH₂—C(CH₃)₂— | CH | 78–79 |

-continued

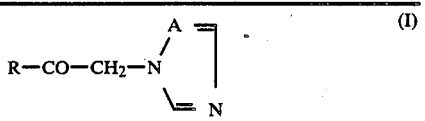

are obtained:

| Example No. | R | A | Melting point (°C.) or refractive index $n_D^{20}$ |
|---|---|---|---|
| 20 | 2-) | N | 1.5441 |
| 21 | 2-) | CH | 127-32 |
| 22 | -O-CH2CH2-C(CH3)2-) | CH | 82-83 |
| 23 | -O-CH2CH2-C(CH3)2-) | N | 101-02 |
| 24 | 2-) | N | 151-53 |
| 25 | NC—CH2CH2—C(CH3)2— | N | 155-58 (× HCl) |

Preparation of a secondary product

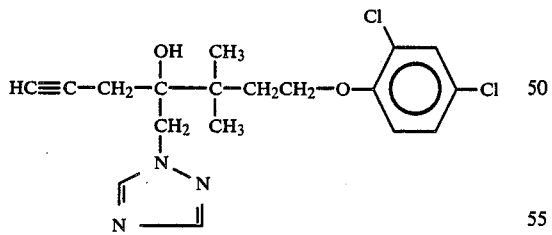

1.58 g (0.058 mol) of aluminum (in the form of flakes) are covered with 7.3 ml of tetrahydrofuran, and a catalytic amount (0.05 g) of mercury(II) chloride and one iodine crystal are added. After standing at 20° C. for 12 hours, 10.3 g (0.087 mol) of propargyl bromide in 11 ml of tetrahydrofuran are added dropwise at 60° C. The mixture is then cooled down to −60° C. and a solution of 17.1 g (0.05 mol) of 5-(2,4-dichlorophenoxy)-3,3-dimethyl-1-(1,2,4-triazol-1-yl)-2-pentanone in 20 ml of tetrahydrofuran is added dropwise. The temperature is allowed to rise to 0° C., this temperature is maintained for a further hour and 22 ml of a saturated aqueous solution of ammonium chloride are added. The mixture is then filtered, the filtrate is evaporated in vacuo and the residue is taken up in 200 ml of ethyl acetate. After washing three times with 100 ml of water each time, the organic phase is dried over sodium sulphate and then evaporated in vacuo. Solvent residues are removed at 50° C. and 0.01 mbar. 14.3 g (74.8% of theory) of 7-(2,4-dichlorophenoxy)-5,5-dimethyl-4-(1,2,4-triazol-1-ylmethyl)-1-heptin-4-ol are obtained as a brownish oil of refractive index $n_D^{20} = 1.5642$.

This compound is fungicidally active and its use is set forth in German application p No. 32 22 191.6 filed June 12, 1982 corresponding to U.S. application.

It will be appreciated that the instant specification and examples are set forth by way of illustration and not limitation, and that various modifications and changes may be made without departing from the spirit and scope of the present invention.

We claim:

1. An azolylmethyl ketone of the formula

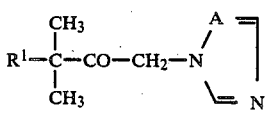

in which

A is a nitrogen atom or the CH group, and $R^1$ is phenoxyethyl optionally substituted by fluorine, chlorine, bromine, methyl, ethyl, isopropyl, tert.-butyl, methoxy, ethoxy, methylthio, trifluoromethyl, trifluoromethoxy, trifluoromethylthio, nitro, dimethylamino, methoxycarbonyl, phenyl and/or chlorophenyl.

2. A compound according to claim 1, wherein such compound is 5-(4-chlorophenoxyl)-3,3-dimethyl-1-(1,2,4-triazol-1-yl)-2-pentanone of the formula

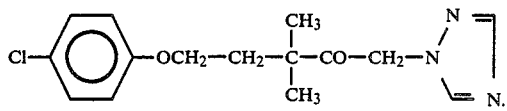

3. A compound according to claim 1, wherein such compound is 5-(2,4-dichlorophenoxy)-3,3-dimethyl-1-(imidazol-1-yl)-2-pentanone of the formula

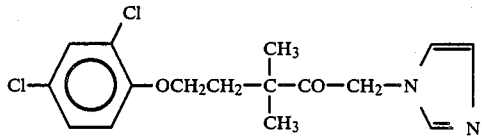

4. A compound according to claim 1, wherein such compound is 4-(4-fluorophenoxy)-3,3-dimethyl-1-(1,2,4-triazol-1-yl)-2-pentanone of the formula

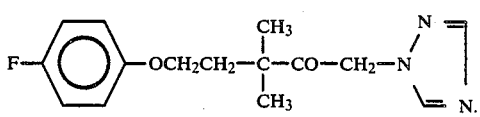

* * * * *

UNITED STATES PATENT AND TRADEMARK OFFICE
CERTIFICATE OF CORRECTION

PATENT NO. : 4,731,452

DATED : March 15, 1988

INVENTOR(S) : Gerhard Jäger, et al.

It is certified that error appears in the above-identified patent and that said Letters Patent is hereby corrected as shown below:

Col. 6, line 6        Delete "O" after "20°"
Col. 8, line 31       Delete "vacupo" and substitute
                      --vacuo--
Col. 12, line 58      Delete "4-(4-" and substitute
                      --5-(4- --

Signed and Sealed this

Eighteenth Day of October, 1988

Attest:

DONALD J. QUIGG

*Attesting Officer*          *Commissioner of Patents and Trademarks*